United States Patent [19]

Devlin et al.

[11] Patent Number: 5,383,472
[45] Date of Patent: Jan. 24, 1995

[54] METHOD AND APPARATUS FOR HANDLING OF BIOPSY TISSUE SPECIMEN

[76] Inventors: Mark T. Devlin; Moustapha B. Zerhouni, both of Computerized Imaging Reference Systems, Inc., 2428 Almeda Ave., Suite 212, Norfolk, Va. 23513

[21] Appl. No.: 94,749
[22] Filed: Jul. 22, 1993
[51] Int. Cl.⁶ ............................................. A61B 5/00
[52] U.S. Cl. ................................... 128/771; 604/403; 378/164; 378/208
[58] Field of Search ................ 128/749, 760, 771; 604/317, 318, 403, 404, 408, 409; 378/163, 164, 208

[56] References Cited

U.S. PATENT DOCUMENTS

| | | | |
|---|---|---|---|
| 3,547,121 | 12/1970 | Cherry | 128/215 |
| 3,940,219 | 2/1976 | Pickett et al. | 604/403 |
| 4,181,859 | 1/1980 | Vitalini | 250/476 |
| 4,474,016 | 10/1984 | Winchell | 62/60 |
| 4,691,333 | 9/1987 | Gabriele et al. | 378/371 |
| 4,728,974 | 2/1988 | Ammerman | 62/4 |
| 4,837,795 | 6/1989 | Garrigus | 378/180 |
| 4,993,056 | 2/1991 | Lary | 378/164 |

*Primary Examiner*—Max Hindenburg

[57] ABSTRACT

A self contained set of imaging apparatus which permit an excised tissue to be handled, inked, imaged in radiology and transported to pathology untouched by human hands. Absolute margins of tissue are inked by solution injected into sealed, disposable bag from syringe attached to the bag. Inked tissue is removed from bag and placed upon fluid-absorbent blotter inscribed with radiographically opaque grid, inside of transparent container. Hinged top and bottom panels of liquid-tight container secure tissue in place. Tissue is visible from outside of container during transport, x-ray imaging, and subsequent pathologic evaluation. Further, the image presented to the pathologist with the inked tissue permits extremely accurate identification of locations of suspect element. The pathologist can easily view the enclosed, undisturbed sample and associated radiograph prior to dissection which can be done within said apparatus if so desired.

18 Claims, 8 Drawing Sheets

METHOD AND APPARATUS FOR HANDLING OF BIOPSY TISSUE SPECIMEN

FIELD OF INVENTION

The present invention relates to a method and apparatus for the post-operative handling of surgical breast biopsy specimens and the radiologic/pathologic localization and analysis of suspect lesions within said specimens.

BACKGROUND DESCRIPTION OF PRIOR ART

Breast cancer has the second highest cancer related death rate among the female population in the United States. This phenomenon has led to greatly increased use of mammography. The ability of mammography to detect suspect lesions has increased significantly since the late 1980's. Heretofore,the use of x-ray mammography coupled with ultrasound and hook and wire devices has improve the pre-operative localization of these suspect lesions. However, substantial inadequacies still exist with regards to the post-operative handling and analysis of surgical biopsy specimens.

One of the most relevant references which has attempted to address some of these inadequacies is Lary, U.S. Pat. No. 4,993,056, which discloses a specimen apparatus consisting of a board with an absorbent square attached thereto, radio-opaque indicia attached in proximity to the absorbent square, a compression sheet hingedly attached to the board and a means for removably attaching the compression sheet and board at a point distal from the hinge. However, close inspection of the radiologic and pathologic procedures for the location and analysis of lesions within a given specimen reveals a number of significant problems with this prior apparatus.

Once delivered to pathology, all surgical biopsy specimens must undergo a process in which the absolute margins of the specimens are painted with a dark indelible pigment such as india ink, tatoo powder or similar dye. Without this procedure which enables the identification of the outer-most edges of the biopsy specimen after sectional cuts are made, the pathologist could not ensure the surgeon that all of the lesion(s) was contained within the margins of the specimen. Regardless of the customary nature by which the pathologist inks a specimen, this procedure requires physical manipulation of the specimen prior to excision of the lesion(s). Because of this manipulation, the specimen is no longer in the same position as when the x-ray image was taken, and the location coordinates ascertained by Lary's device are thus rendered useless.

In addition, Lary teaches that the radio-opaque indicia consist of strips of copper with letters and numbers punched out. These strips are then attached to the adjoining edges of the absorbent square. The apparatus of Lary does not have grid lines throughout. This requires the radiologist to make a visual approximation of the lesion location from the indicia which may be quite distant from the lesion (up to 4 inches). The preciseness of an x-ray coordinates ascertained from this prior device is subject to question because in many instances the very suspect tissue may be no more than a series of micro-calcifications each having a diameter of less than 200 microns.

Lary also teaches that the board and compression sheet be comprised of a sandwich structure having an expanded polystyrene core and paper laminated to both sides of said core. Because the material specified for construction is opaque in nature, it is impossible to visually inspect the specimen within the device and thus a "focusing target" is required on top of the compression sheet of this prior device. Regardless of the addition of a target, without opening the hinged device and exposing the specimen, one cannot assure the exact location of the specimen on the absorbent blotter,cannot inspect the physical size of the specimen to determine appropriate kilo Voltage peak (kVp) and milli-Amperes per second (mAs) settings for imaging, and cannot visually inspect the specimen during compression to achieve optimal compression.

The specimen-holding apparatus of Lary, in and of itself, does not permit containment of fluids associated with specimens. This short fall requires that Lary's apparatus be placed in a clear polyethylene resealable bag which further impedes inspection of the specimen prior to imaging and can result in the possible dispersement of specimen fluids to the outer surfaces of the apparatus contained therein. With the present widespread concern about prevention of infection from blood-borne pathogens, proper containment of unidentified bodily fluids creates emotional as well as practical problems.

Lary's device further comprises a writing surface with diagrams which is separate from the primary apparatus designated for containment of the specimen. This presents the possibility for confusion of specimen identity and, ultimately, patient diagnosis.

Another reference to be noted is Garrigus, U.S. Pat. No. 4,837,795, which discloses a tissue specimen holding device consisting of three platens preferably fabricated from acrylic sheet measuring 0.25 inches, 0.50 inches and 0.25 inches respectively. Said platens are typically joined by nut and bolt assemblies, allowing the platens to be drawn towards one another "to compress the tissue specimen prior to radiographic exposure to squeeze excess fluids from the specimen and to flatten it to have substantially the same overall thickness and density." One of said platens contains a grid, dividing it into a plurality of regions. The grid is preferably fabricated from radio-opaque tape.

Several problems are associated with prior tissue specimen holding devices made in accordance with the Garrigus reference. The device of Garrigus is non-disposable. It requires cleaning and sterilization. The chance for foreign artifacts to be present in any radiographic image is increased. The possibility of cross contamination from specimen to specimen also exists. This prior device,like that of Lary, in and of itself, does not contain the fluids which are inherently associated with any surgical specimen. Any point of reference established through employment of Garrigus grid is lost when the specimen must be manipulated for pathologic examination. Because patient marking labels are not directly attached to the container in such prior devices, confusion of specimen identity may result. This prior device is equipment dependent,and special fabrications may be required depending on the size and shape of the mammographic film holder and compression paddle of any particular machine. In addition, this prior device comprises one inch of acrylic, which necessitates relatively high kVp setting in order to achieve proper exposer. This relatively high kVp in conjunction with the thickness of the device results in a high level of back-scatter radiation, and ultimately results in low contrast and reduced detail resolution-both of which are critical to image evaluation.

Vitalini, U.S. Pat. No. 4,181,859 discloses a grid which is preprinted with radio-opaque ink and then attached to the x-ray film prior to exposure to enable two dimensional measurement of the x-ray image. It is adapted for use with flexible radiographic films commonly used in dentistry. This device allows the archival of a two dimensional measurement while the film undergoes considerable deformation commonly associated with dental exposures.

Another reference is Cherry, U.S. Pat. No. 3,547,121 which describes a radio-opaque grid for use with x-ray positioning and needle placement for fetal transfusions. Said grid is placed on the abdomen of the pregnant patient to aid in the location of the fetus to receive the needle from within the peritoneal cavity.

A further referenced is Gabriele et al. U.S. Pat. No. 4,691,333 which discloses a perforated strap compression device used for needle localization in conjunction with a mammography film cartridge.

Another reference is Ammerman, U.S. Pat. No. 4,723,974 which discloses a flexible container which provides a cool compartment for the transport of amputated extremities.

A similar reference is Winchell, U.S. Pat. No. 4,474,016 which discloses a sterile cooling system for organs during transplant operations.

Yet another reference is Bliss, U.S. Pat. No. 2,399,424 which discloses measurement indicia on the side of x-ray film to determine foot size for the fitting of shoes.

SUMMARY OF THE INVENTION

Accordingly, a principal object of the present invention is to provide a product which addresses all the foregoing problems associated with standard biopsy procedure.

It is an object of this invention to provide an inexpensive disposable device in which a tissue specimen's absolute margins are inked within a self contained system prior to placement in an imaging container, thereby eliminating the necessity for physical manipulation of the specimen in pathology prior to excision of suspect tissue and subsequently empowering the full advantages of a radio-opague grid and lesion coordinates obtained in radiology.

It is an object of this invention to provide an inexpensive, resealable, fluid-tight, transparent, disposable "clamshell" container for the post-surgical handling and radiographic imaging of surgical biopsy specimens.

It is another object of this invention to provide a container of the character described which allows continuous visual inspection of any specimen contained within the closed imaging container, thus enabling: accurate positioning and focusing of x-ray equipment; assessment of specimen size to determine proper kVp/mAs settings; and observation of specimen during compression to obtain optimal pressure and uniform specimen thickness and visual assurance that specimen does not move within the container prior to pathologic workup.

It is a further object of this invention to provide an imaging container which is completely fluid tight in and of itself, thus negating the need for any additional containers or fluid tight envelopes, and eliminating any risks associated with exposure to specimen fluids for those involved in transport or radiographic analysis of biopsy specimens.

It is another object of this invention to provide both a radio-opaque grid with lines in markedly small increments and indicia imprinted directly to an absorbent blotter which lies under the specimen. It is another object of the present invention to provide a device of the character described wherein the container bottom, blotter and grid are of minimal thickness, such that the need for increased kVp is eliminated and the distance between the specimen and the screen film is substantially reduced. It is another object of the present invention to provide a device of the character described wherein enlargement distortions, shadowing and other similar problems associated with the prior art are minimized.

It is another object of this invention to provide a device of the character described wherein communication accuracy is improved between radiology and pathology as to the exact location of suspect tissues within a specimen. It should be noted that unlike usual tissue biopsies from other parts of the human anatomy where the growth is relatively finite and discernable to the human eye, in the case of mammography, the tissue being examined may be little more than calcification within ductile tissue—tell tale calcification of 100–200 microns in size being typical. Thus, there is a need for extremely accurate localization techniques.

It is another object of this invention to have patient information labels permanently adhered directly to the containers to avoid any possible confusion associated with handling and transport of biopsy specimens.

It is another object of this invention to increase efficiency and reduce overall costs associated with surgical biopsy procedures and radiologic/pathologic analysis of biopsy specimens.

Further objects and advantages of our invention will become apparent from a consideration of the drawings and ensuing description of it.

DESCRIPTION OF INVENTION

Figure 1:
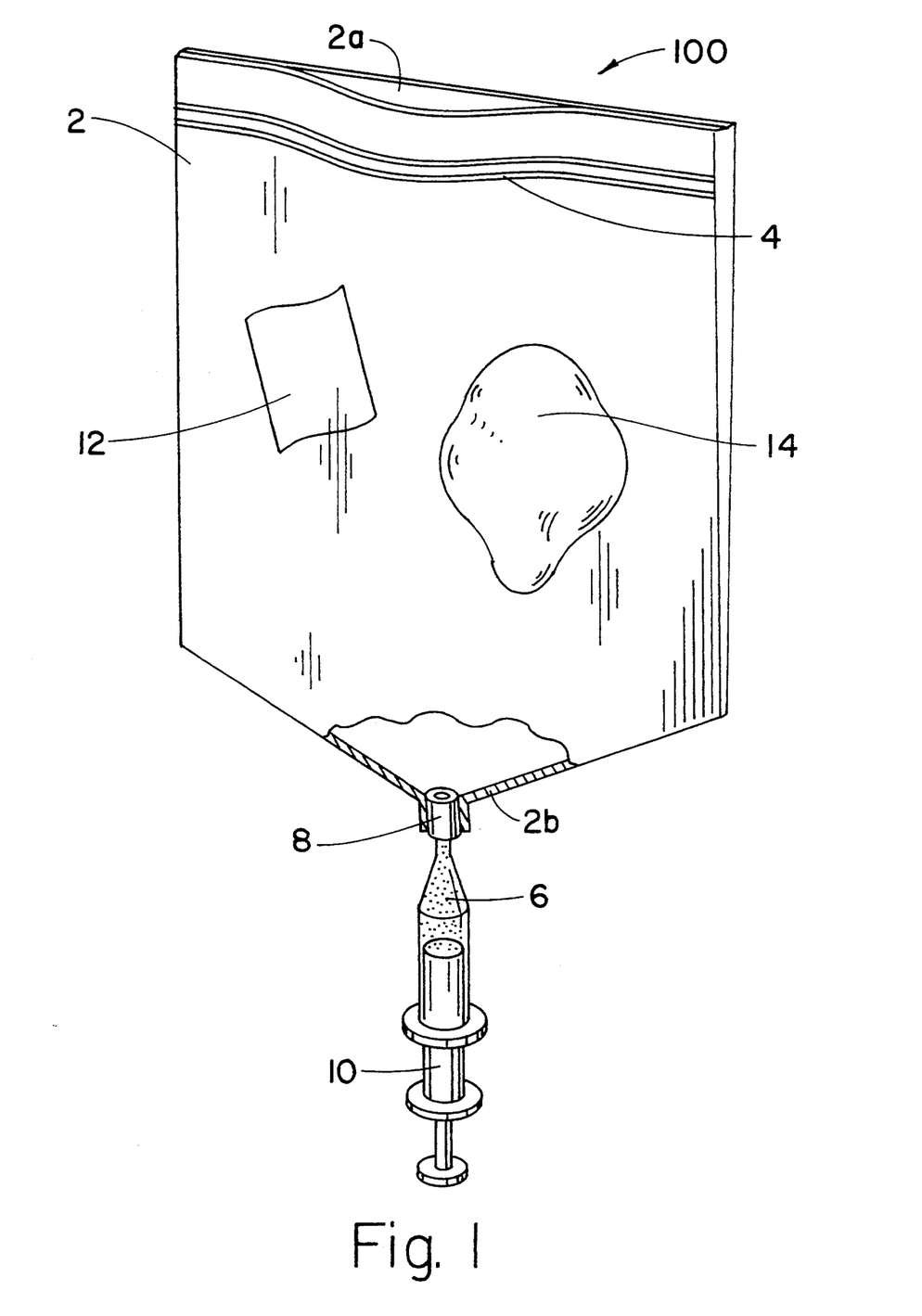
FIG. 1 is a perspective view of the self contained inking device.
Figure 3:
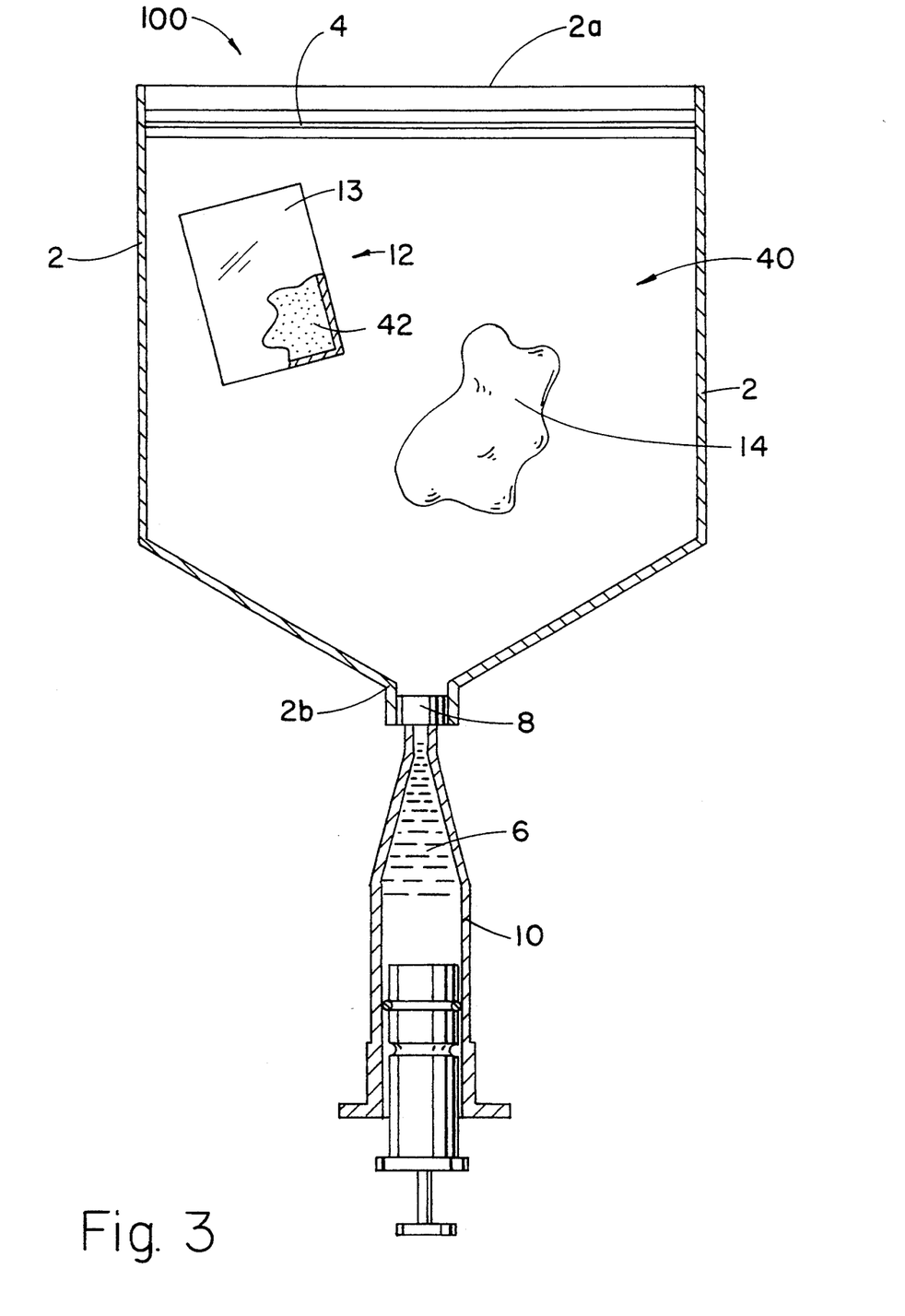
FIG. 3 is a medial cross-sectional view of the self-contained inking device of the present invention.

FIGS. 1 and 3 show an inking assembly, (generally designated 100), which is specifically designed to facilitate the inking of the absolute margins of tissue specimen 14immediately after its surgical removal from a patient without requiring extensive handling of the specimen 14. The inking assembly 100 comprises a polyethylene bag 2 which measures approximately 5"×5" with one open end 2a, into which may be placed a tissue specimen 14, and which can be temporarily sealed via zip, twist tie or similar closure device 4. Enclosed within an interior compartment 40 of the bag is an absorbent insert (generally designated 12) consisting of a paper envelope 13 containing a hygroscopic gel 42 capable of absorbing specimen fluids and excess pigment. Adjoined to said bag 2 is a syringe 10 filled with a special solvent-based, fast drying pigment 6 which, when injected into the bags interior compartment 40, will not diffuse to inner portions of the specimen 14. The syringe 10 is joined to the bag 2 via a valve 8 which is disposed at a second end 2b of the bag.

Figure 2:
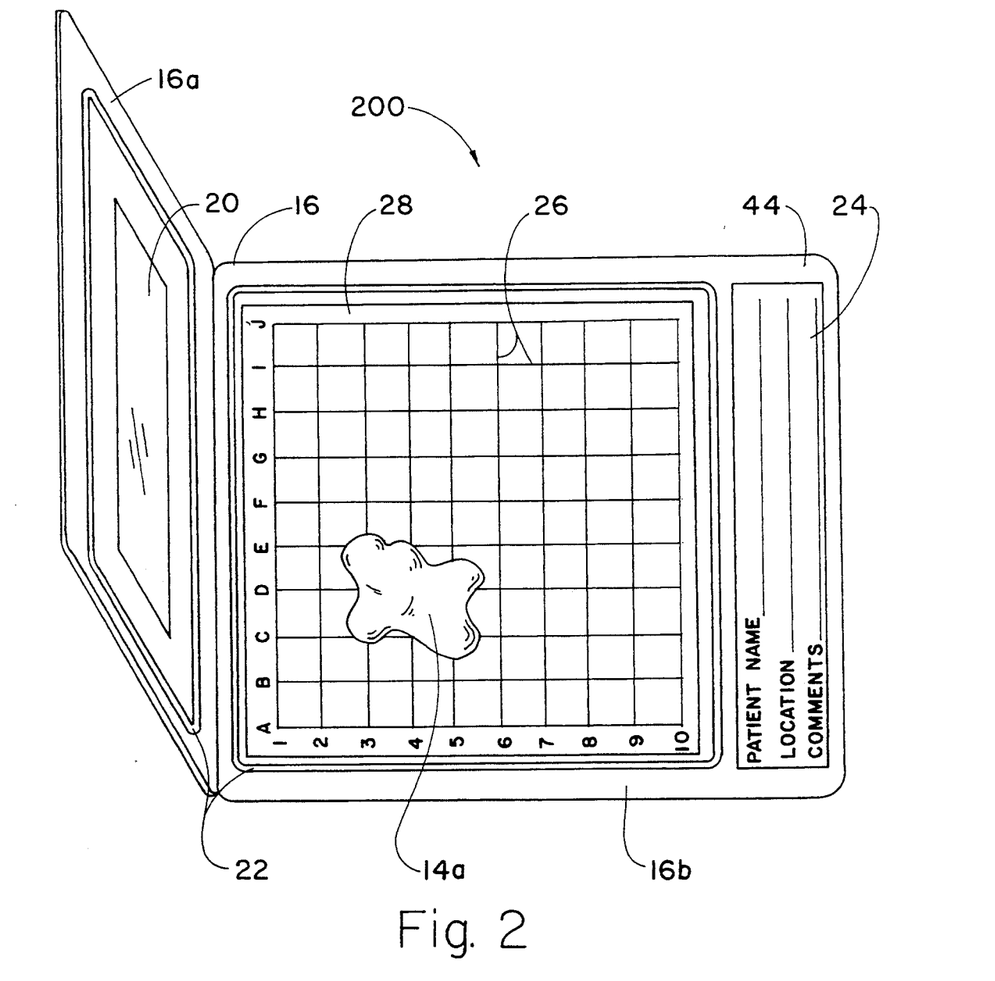
FIG. 2 is a perspective view of the present invention, showing the translucent transport and imaging container in an open position with optional cutting window, the blotter, grid and patient information label.

FIG. 2 shows an imaging transporter assembly (generally designated 200). The imaging transporter assembly 200 comprises a clamshell-like hinged container 16, which preferably measures approximately 6"×6"×1/8" in its entirely and is made of a transparent pvc or similar plastic sheet which is approximately 0.004" to 0.020" thick. The container 16 comprises an upper panel 16a and a lower panel 16b. Within the container 16 there is placed a layer of absorbent material 28 preferably made of paper. A radiographically opaque grid 26 with x y coordinates is silk-screened directly to said paper; the ink is preferably a black acrylic ink containing at least 50% Bismuth Oxide powder by weight. The container 16 may be latched shut by use of a closure mechanism 22 which surrounds the boarders of the container. Once shut the container 16 is fluid tight, transparent and able to remain closed even under slight pressure from within. The upper panel 16a maybe provided with an optional window 20 made of thin transparent film affixed to the pvc upper panel 16a to facilitate dissection of the specimen 32 disposed within the closed container 16 by allowing a cutting blade (not shown) to pass easily through the imaging transporter assembly 200 while simultaneously slicing the inked specimen 14a contained therein. At the lower end of the container 16 is an extension 44 of the upper panel 16a which has a patient information label 24 permanently attached to it for recording all pertinent patient and specimen information.

OPERATION OF THE PREFERRED EMBODIMENT OF THE INVENTION

Although the present invention has application in many common pathologic scenarios, for simplicity its application to breast biopsies will be described. However, it is within the scope of the present invention to employ the disclosed apparatus and method in the handling, x-ray imaging and localization of suspect tissues other than just breast tissues.

Referring now to FIGS. 1 and 3: A surgeon first removes a tissue specimen 14 from a patient. The specimen 14 is then placed inside the polyethylene bag 2 through the re-closable open end 2a of the bag. The polyethylene bag 2 is then sealed shut with the closure device 4. With the specimen 14 in the interior compartment 40 of the bag, a syringe 10 is used to inject the special pigment 6 into the interior compartment 40 of the bag. The bag 2 and the specimen 14 sealed therein are then kneaded so as to fully coat the specimen with the special pigment 6. Excess pigment 6 is then extracted via the syringe 10 and the absorbent insert 12.

The closure device 4 is then re-opened, and the "inked" (i.e. pigmented) specimen is removed from the polyethylene bag 2 for placement in the imaging transporter assembly 200. Once the specimen 14 has been removed from the polyethylene bag 2 the bag is closed before discarding to insure proper containment of any specimen residue which can be considered bio-hazardous waste. Once properly closed, the inking assembly 100 is discarded.

Figure 4:
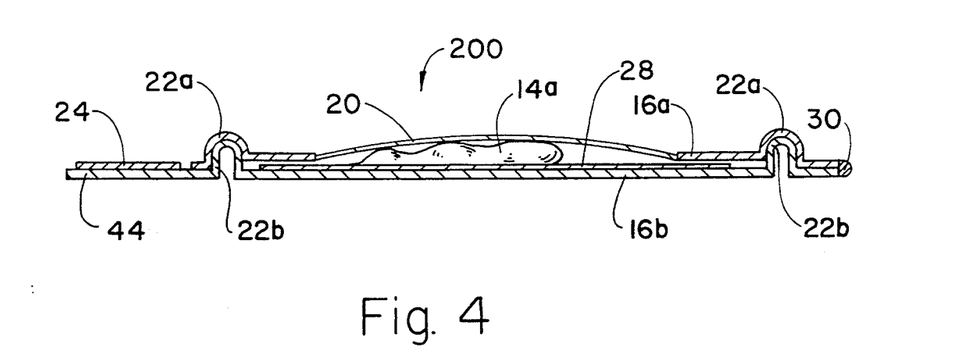
FIG. 4 is a cross-sectional view of the translucent transport and imaging container of the present invention in the closed position.
Figure 5:
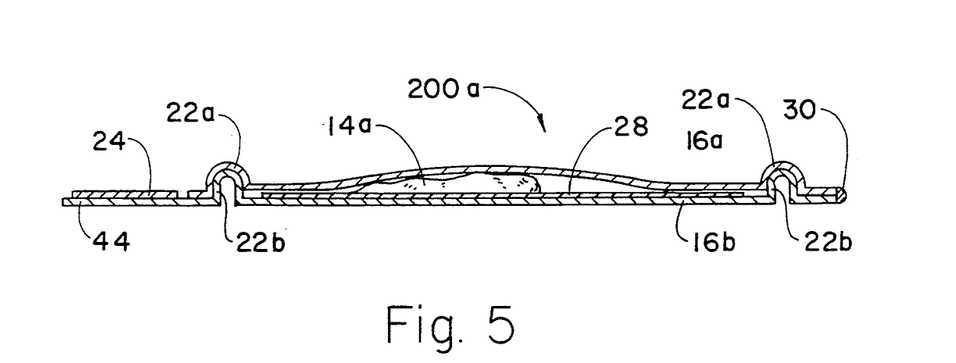
FIG. 5 is a cross-sectional view similar to FIG. 4 showing a modified transport and imaging container.

Referring now to FIGS. 2 and 4: The container 16 of the imaging transporter assembly 200 is opened and the "inked" specimen 14a is placed upon the absorbent material 28 within the boundary of the radiographically opaque grid 26. The container 16 is then closed,with the film window 20located in the top panel 16a of the container pressing the inked specimen 14a against the absorbent material 28 and thereby holding the specimen in place. In the preferred embodiment of the invention the closure mechanism 22 comprises an endless male ridge 22b in the lower panel 16b of the container and an endless female ridge 22a in the upper panel 16a of the container. When the endless male ridge 22b is properly nested inside the endless female ridge 22a the container 16 is sealed shut. In addition to sealing the specimen 14a inside the container 16, the closure mechanism 22 also provides a physical barrier which confines liquid (such as may emanate from the compressed specimen) within the container. The endless male ridge 22b also provides a convenient positioning device for placement of the absorbent material 28 during assembly, and assists in maintaining the position of the absorbent material 28 (and, therefor, any specimen adjacent thereto) during use of the device.

With the inked specimen secured inside of the closed container 16, the imaging transporter assembly 200 (and the specimen 14a) may now be safely and conveniently transported to the hospital's radiology department ("radiology").

In radiology, a mammographic image of the inked specimen 14a is taken while the specimen 14a is in place inside of the (closed) imaging transporter assembly 200 which can be compressed by the mammographic x-ray machine to desired thickness. The radiologist then immediately reports his or her findings based on the x-ray image taken so the surgeon can complete the operation, and sends the film image and the specimen 14a (which is still positioned against the gridded absorbent material 28, inside container 16) to the hospital's pathology department ("pathology"), along with notation on the attached label 24 regarding the exact coordinates of the lesion.

The pathologist receives the imaging transporter assembly 200 (containing the inked specimen 14a), the x-ray film(s) showing the image of the specimen and the accompanying notations pertaining to lesion coordinates. With the specimen 14a still lying in place on the gridded absorbent material 28, excision of the suspect tissues can be conducted through the film window 20, without removing the specimen from the container 16. Alternatively, the container 16 may be opened and the excision conducted directly upon the exposed specimen by customary procedures.

Figure 6A:
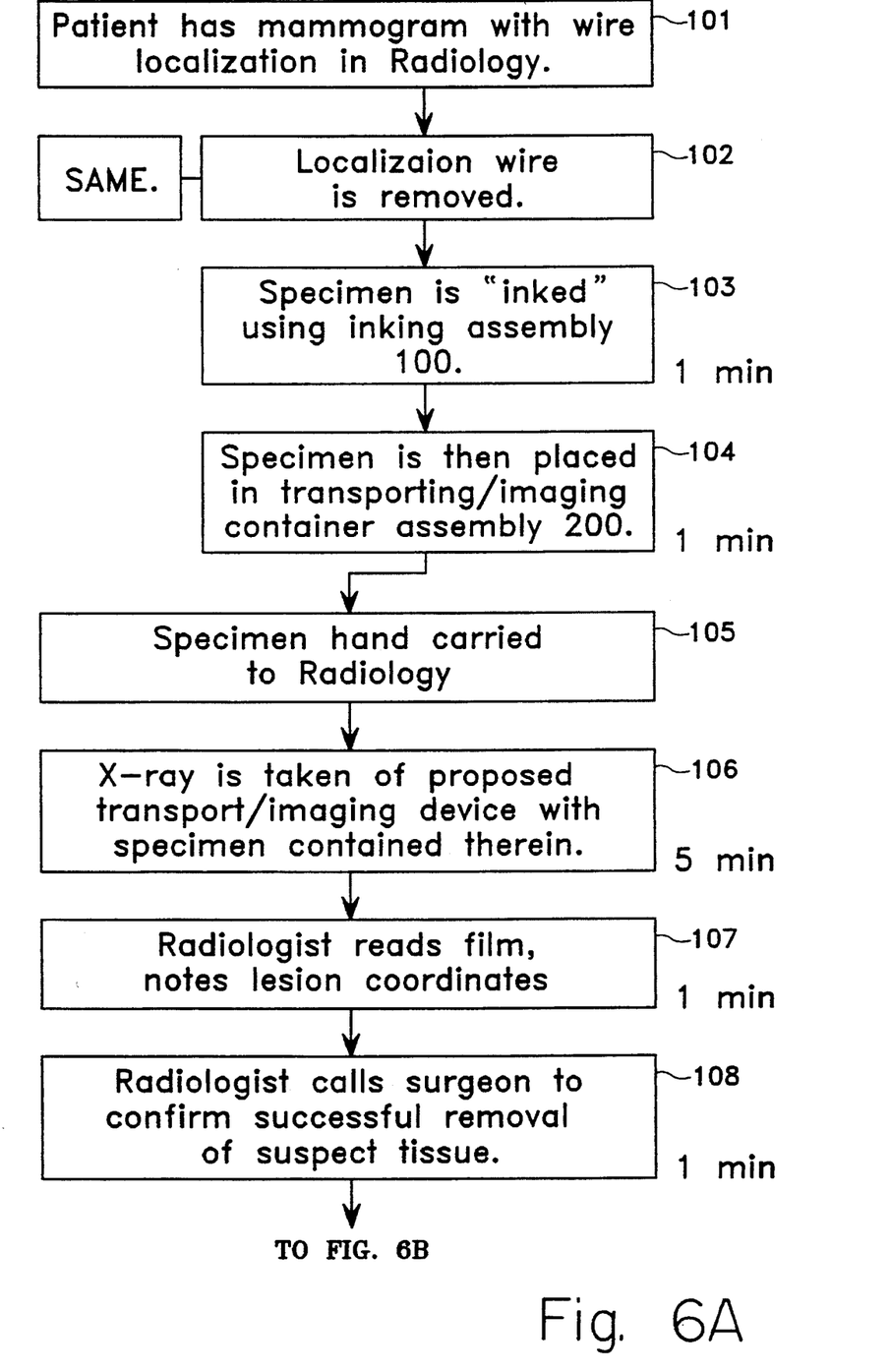
FIG. 6 is a flow chart illustrating the preferred method for handling of biopsy tissue specimens in accordance with the present invention.
Figure 6B:
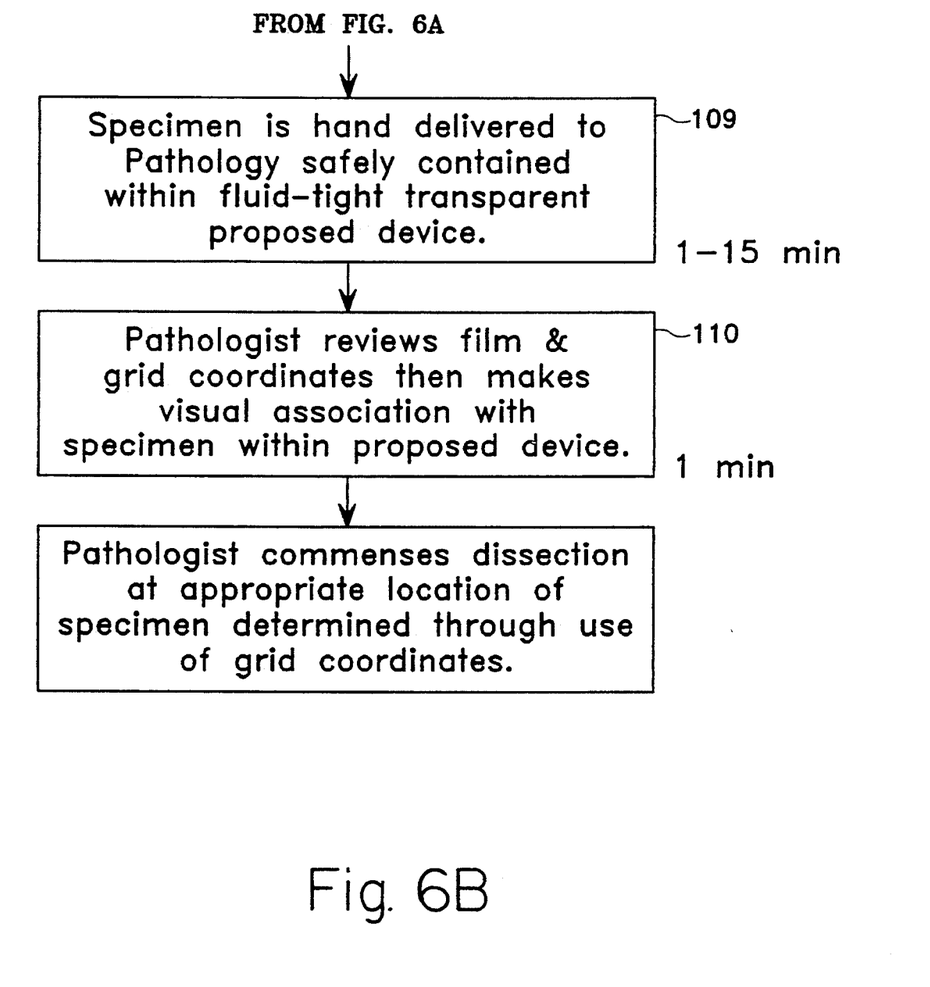
Figure 7A:
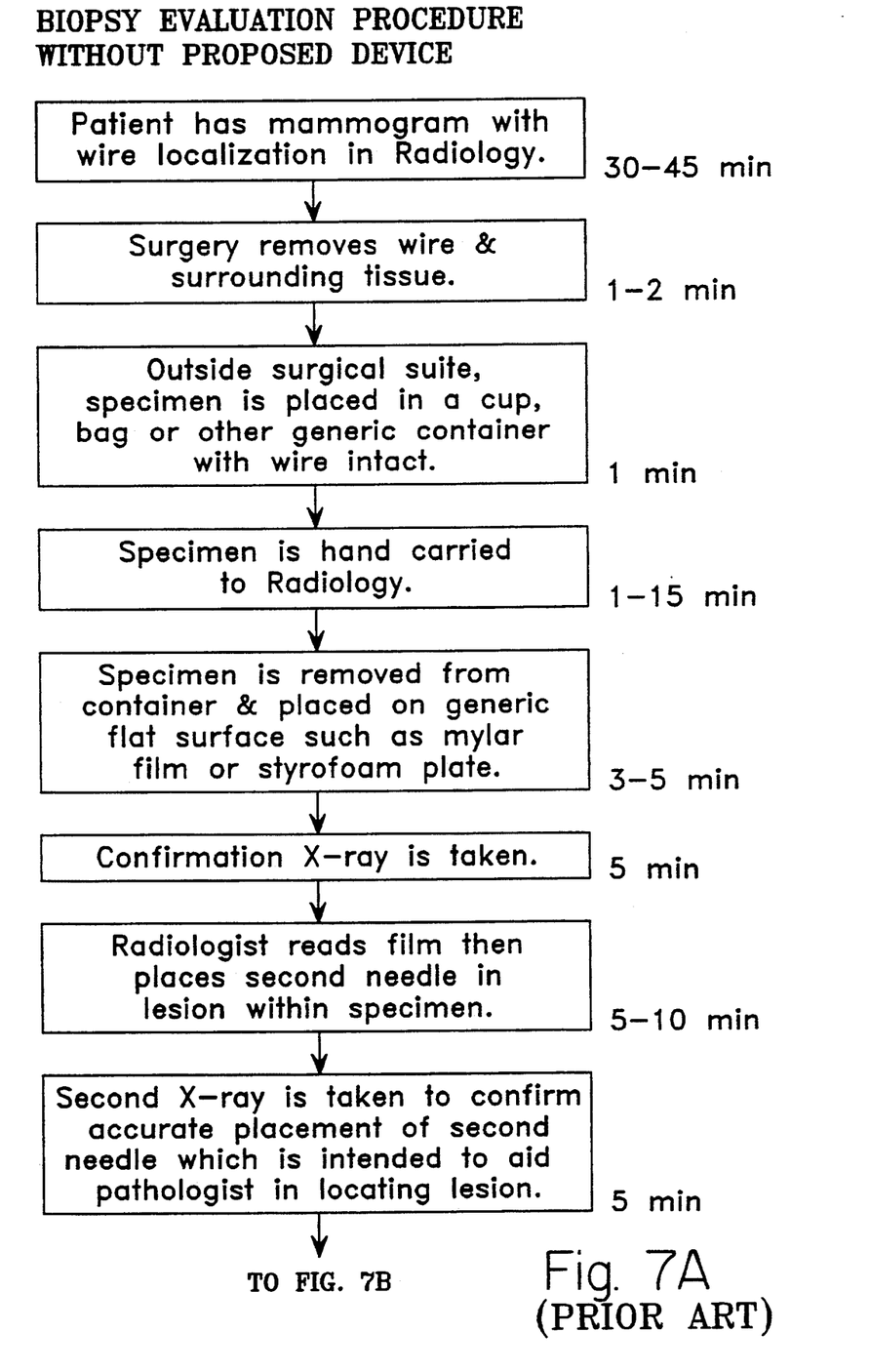
FIG. 7 is a flow chart illustrating a prior method of handling biopsy tissue.
Figure 7B:
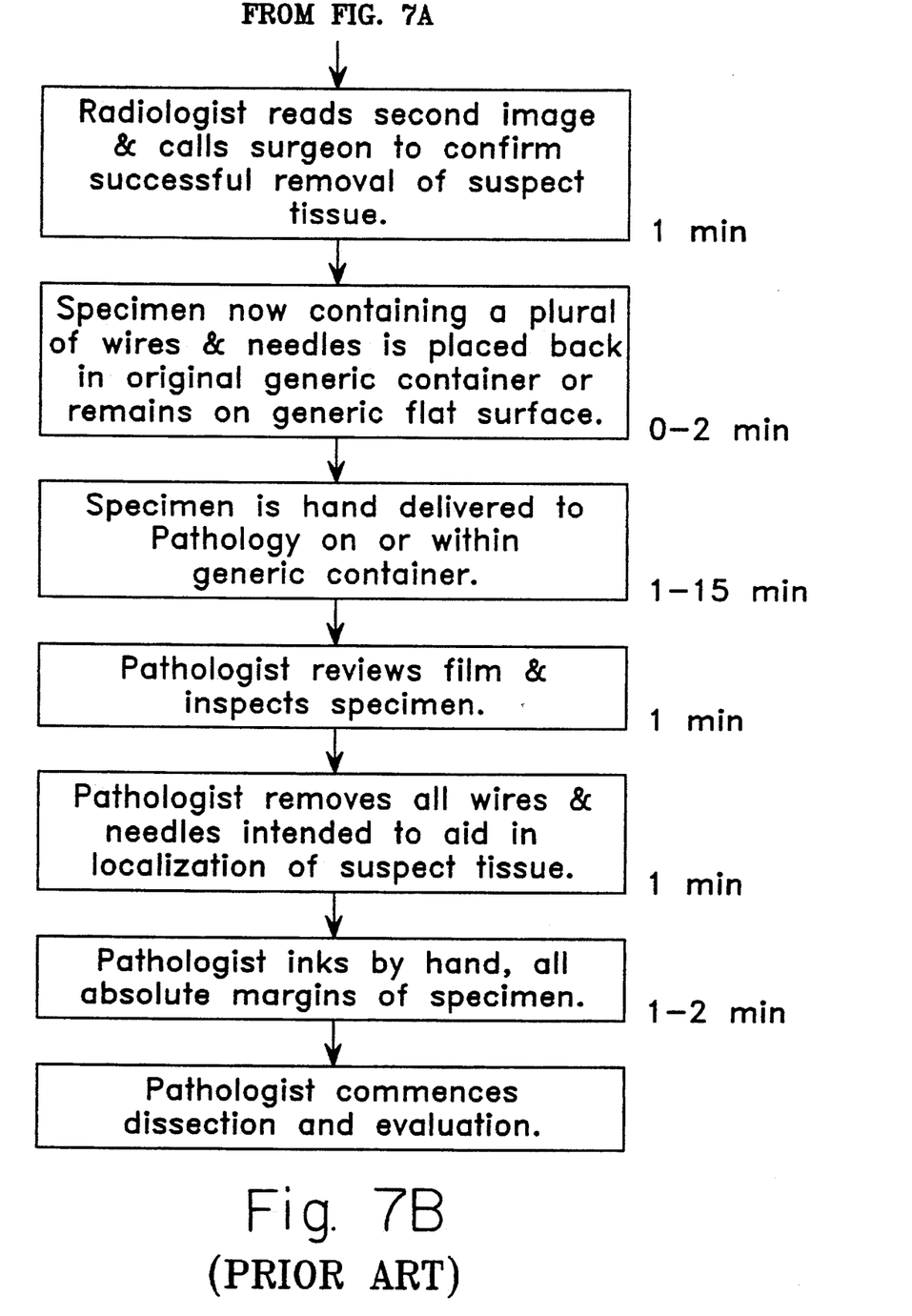

It will be appreciated by those skilled in the art that the apparatus constructed in accordance with the disclosed invention facilitates a novel method of handling and evaluating biopsy tissue specimens which is more efficient, more safe and less time consuming than prior methods of biopsy evaluation. FIG. 6 schematically illustrates the process for evaluating biopsies in accordance with the preferred embodiment of the present invention. For purposes of comparison, FIG. 7 schematically illustrates the common method of prior biopsy evaluations.

Referring now to FIG. 6: The patient has a mammogram taken 101 to enable wire localization in Radiology. Surgery removes tissue surrounding the lesion and localization wire 102. The specimen is then "inked" 103 using the inking assembly (100) described above. This inking typically takes approximately one minute. The inked specimen is then placed 104 in the transporting and imaging container assembly (200)—a step which may take up to one minute. The enclosed specimen is then hand carried 105 to Radiology which can take any where from one to fifteen minutes depending on the distance between departments. In Radiology the specimen can be compressed within the transporting and imaging container and an x-ray image is taken 106. Typically five minutes is more than sufficient time for an image to be obtained. The Radiologist then reads 107 the film and notes grid coordinates of the element to be excised from the specimen in pathology. Time required to read the film depends on the radiologist but is often under several minutes. After reading the film the radiologist notifies 108 the surgeon as to the status of the patient ie. "was the suspect tissue was successfully removed"). Notification is often by telephone and requires only seconds. The enclosed specimen is then hand delivered 109 to Pathology with the accompanying x-ray image for analysis. Once again this step can take any where from one to fifteen minutes depending on the proximately of departments. The pathologist reviews 110 the film and makes a visual association with specimen contained within the proposed device. This typically will take only seconds. At this point the pathologist will take the necessary steps to extract the suspect tissue from the specimen and make a diagnosis (malignant or benign). As previously mentioned, time required for the pathologist to extract the suspect tissue from the specimen is substantially less than prior methods because inking is no longer done by pathology and specific location coordinates are provided to aid in finding the suspect tissue.

It will be appreciated by those skilled in the art that apparatus for handling biopsy tissue specimens constructed in accordance with the above disclosure provides a means of substantially reducing imaging turnaround time (and subsequent surgery time) by streamlining and improving overall efficiency of current procedures for the handling, transport and evaluation of surgical biopsy specimens.

It will be appreciated by those skilled in the art that apparatus for handling biopsy tissue specimens constructed in accordance with the above disclosure provides a means of safely handling and transporting biopsy specimens within and between various departments of a hospital. It will be understood that the entire operation of "inking" the specimen, transporting the specimen, imaging the specimen, and excising the lesion from the specimen is conducted while the specimen is safely protected within either the polyethylene bag 2 or the container 16.

Comparison of FIGS. 6 and 7 make evident the fact that the proposed invention substantially reduces procedural time which can result insubstantial cost savings to medical institutions currently performing such biopsy procedures.

It will also be appreciated by those skilled in the art that apparatus for handling biopsy tissue specimens constructed in accordance with the above disclosure greatly improves accuracy and efficiency of pathologic extractions of suspect tissues within a given specimen. It will be understood that a specimen can be successfully "inked" prior to x-ray imaging thus the pathologist will no longer be required to physically manipulate the specimen prior to excision of lesion(s). It will also be understood that this allows visual references ascertained through use of grid coordinates to be properly employed.

It will also be appreciated by those skilled in the art that apparatus for handling biopsy tissue specimens constructed in accordance with the above disclosure allows for continuous visual inspection of any specimen contained therein. It will understood that being able to see a specimen within such apparatus allows for the accurate positioning of said specimen for mammographic x-ray imaging. It will also be understood that being able to see a specimen within such apparatus allows for the safest means of assessing specimen size which is necessary for determining kVp and mAs settings. It will also be understood that being able to see a specimen within such apparatus allows one to continuously monitor the level of specimen compression and obtain optimal pressure prior to x-ray exposure and thus improving image detail.

It will also be appreciated by those skilled in the art that apparatus for handling biopsy tissue specimens constructed in accordance with the above disclosure provides a radio-opaque grid with sufficient detail for accurately locating suspect tissues. It will be understood that cancerous lesions can be as small as 150 micron size as is the case with some micro-calcification within ductile tissues. Thus a grid which is a minimal distance from the screen film (eliminating distortions) and has extremely fine details will allow a much more accurate assessment of lesion coordinates and eliminate the need for estimations or generalizations as to location.

It will also be appreciated by those skilled in the art that apparatus for handling biopsy tissue specimens constructed in accordance the above disclosure provides an extremely simple and inexpensive means of transporting and pathologically evaluating surgical biopsy specimens.

While the above descriptions contain many specificities, these should not be construed as limitations on the scope of the invention but rather as one preferred embodiment thereof. Many other variations are possible. For example, the inking bag could be made of vinyl or any other fluid impermeable material for disposable bag fabrication. The ink reservoir may alternatively comprise a temporary fluid containment system such as breakable vile, or plastic pouch, etc., in place of the syringe. Although a special fast drying pigment is identified, any pigment which stains the outer margins of the specimen and is not absorbed to the inner tissue would be suitable. With regards to the imaging container, it can be manufactured from any thin semi-rigid, transparent material suitable for therm-o-forming applications. The absorbent blotter can be made from any material with adequate absorbent characteristics such as paper, cloth or sponge. The radiographically-opaque ink can be made from any combination of screening ink and additive containing substantial x-ray attenuation characteristics to include but not be limited to bismuth oxide, bismuth powder, lead oxide, lead powder and iodine. The film window can be made from any film which is inelastic and has low deformation characteristics but is easy to penetrate and cut with a sharp blade. The information, bio-hazard label(s) etc., can be attached virtually any where on the containers where they do not inhibit visual inspection of the enclosed specimen. This invention need not be limited to that of breast biopsy but can be used in any pathologic scenario in which x-ray imaging and localization techniques prove advantageous. Accordingly, the scope of the invention should be determined not by the embodiments illustrated but by the claims and their legal equivalents.

We claim:

1. A specimen handling apparatus comprising:
    a closeable first container;
    wherein said first container comprises a top member and a bottom member, and further comprising an interior chamber between said top member and said bottom member when said first container is in a closed position;
    said top member of said first container having a top surface and a bottom surface and a first edge; and,
    said bottom member of said first container having a top surface and a bottom surface and a first edge;
    hinge means for attaching said first edge of said top member of said first container to said first edge of said bottom member of said first container;
    a specimen blotter member disposed adjacent said top surface of said bottom member of said first container;
    said specimen blotter member comprising a fluid-absorbent material and having a substantially flat top surface;
    a radiographically opaque grid attached to said top surface of said specimen blotter member;
    first sealing means by which said interior chamber of said first container is made liquid-tight when said top member of said first container is in a closed position;
    said interior compartment of said first container being adapted to contain a specimen between and in contact with said top surface of said specimen blotter member and said bottom surface of said top member of said first container when said first container is in a closed position;
    wherein said top member of said first container comprises either a transparent or a translucent material, such that said grid attached to said top surface of said specimen blotter is visible when said first container is closed;
    and wherein said sealing means comprises;
    an endless convex ridge on said top surface of said bottom member of said first container;
    and an endless concave groove on said bottom surface of said top member of said first container;
    wherein said endless convex ridge is adapted to mate with said endless concave groove when said first container is in a closed position;
    and wherein said endless convex ridge encircles said specimen blotter member;
    and further comprising a resealable, liquid impermeable second container;
    an absorbent member disposed within said second container;
    and means to introduce pigment into said second container.

2. The invention according to claim 1, wherein said means for introducing pigment into said second container comprises a syringe.

3. The invention according to claim 1, wherein said means for introducing pigment into said container comprises a breakable vial, capsule, or bag.

4. The invention according to claim 1 wherein said pigment is a solvent based fast drying ink.

5. The invention according to claim 1 wherein said pigment is india ink.

6. The invention according to claim 1 wherein said pigment is tattoo powder or a tattoo powder emulsion.

7. A method of handling tissue specimen comprising the steps of:
    placing said specimen inside a hinged first container on top of a fluid-absorbent specimen blotter member within an outside boundary of a radiographically opaque grid attached to the top of said blotter member;
    closing atop member of said first container against said specimen and against a bottom member of said first container so as to completely enclose said specimen within a liquid-tight transparent compartment in said first container; and,
    visually observing the position of said specimen relative to said grid from outside of said first container after said container is in a closed position;
    and further comprising producing an x-ray film of said specimen and said grid while said specimen is within said liquid-tight compartment of said first container;
    and further comprising reading said x-ray film of said specimen and said grid; and recording the position, relative to the grid in said film, of an image of a finite element of said specimen shown in the image of said specimen;
    and further comprising locating said finite element of said specimen, corresponding to said image of said finite element in said x-ray film, while said specimen is enclosed within said liquid-tight compartment of said first container;
    and further comprising inserting said specimen within an interior chamber of a sealable second container prior to said step of placing said specimen inside a hinged first container;
    sealing said specimen within said second container;
    introducing pigment into said second container;
    applying said pigment to said specimen while said specimen is sealed within said second container; and,
    subsequent to said step of applying said pigment to said specimen, removing a portion of said pigment from said interior chamber of said sealable second container while said second container is sealed; and,
    removing pigmented specimen from said second container.

8. The method according to claim 7, wherein said step of introducing pigment into said second container comprises:
    ejecting said pigment from a syringe attached to said second container.

9. The method according to claim 7, wherein said step of removing a portion of said pigment from said interior chamber comprises:
    absorbing said pigment into an absorbent device disposed within said second container.

10. The method according to claim 7, wherein said step of removing a portion of said pigment from said interior chamber comprises:
    withdrawing said portion of said pigment into said syringe.

11. A specimen imaging and handling apparatus comprising:

a closeable first container;

wherein said first container comprises a top member and a bottom member, and further comprising an interior compartment between said top member and said bottom member when said first container is in a closed position;

said top member of said first container having a top surface and a bottom surface and a first edge; and said bottom member of said first container having a top surface and a bottom surface and a first edge;

hinge means for attaching said first edge of said top member of said first container to said first edge of said bottom member of said first container;

a specimen blotter member disposed adjacent to said top surface of said bottom member of said first container;

said specimen blotter member comprising a fluid-absorbent material and having a substantially flat top surface;

a radiographically opaque grid attached to said top surface of said specimen blotter member;

wherein said first container comprises a first sealing means by which said interior chamber of said first container is made liquid-tight when said top member of said first container is in a closed position;

said interior compartment of said first container being adapted to contain a specimen between and in contact with said top surface of said specimen blotter member within said finite perimeter of said opaque grid and adjacent to said opaque grid, and said bottom surface of said top member of said first container when said first container is in said closed position; and, wherein said top member of said first container comprises either a transparent or a translucent material, such that said grid attached to said top surface of said specimen blotter is visible when said first container is in said closed position.

12. The invention according to claim 11, wherein said sealing means comprises;

an endless convex ridge on said top surface of said bottom member of said first container;

and an endless concave groove on said bottom surface of said top member of said first container;

wherein said endless convex ridge is adapted to mate with said endless concave groove when said first container is in a closed position;

and wherein said endless convex ridge encircles said specimen blotter member.

13. The invention according to claim 12, wherein said radiographically opaque grid comprises silk screen ink and a radio-opaque first material.

14. A method of handling tissue specimen comprising the steps of:

placing said specimen inside a hinged first container on top of a fluid-absorbent specimen blotter member within an outside boundary of and adjacent to a radiographically opaque grid attached to the top of said blotter member;

closing atop member of said first container against said specimen and against a bottom member of said first container so as to completely enclose said specimen within a liquid-tight transparent compartment of said first container; and, visually observing the position of the specimen relative to said grid from outside of said first container after said container is in a closed position.

15. The method according to claim 14, further comprising:

producing an x-ray film of said specimen on said grid while said specimen is within said liquid-tight compartment of said first container.

16. The method according to claim 14, further comprising;

reading said x-ray film of said specimen on said grid; and, recording the position, relative to the visible grid in said film, of an image of a finite element of said specimen shown in the image of said specimen.

17. The method according to claim 16, further comprising:

locating said finite element of said specimen, corresponding to said image of said finite element in said x-ray film, while said specimen is enclosed within said liquid-tight compartment of said first container.

18. The method according to claim 17, wherein the step of recording the position, relative to the grid in said x-ray film, of an image of a finite element of said specimen shown in the x-ray of said specimen comprises:

writing patient information and information indicative of the grid coordinates of said finite element on an outside area of said container such that said written information and said specimen are simultaneously observable when said specimen is enclosed within said liquid-tight, transparent compartment of said first container.

* * * * *